(12) United States Patent
Ishihara et al.

(10) Patent No.: US 10,712,421 B2
(45) Date of Patent: Jul. 14, 2020

(54) MRI APPARATUS WITH RF CORRECTED EACH TR INTERVAL

(71) Applicant: TOSHIBA MEDICAL SYSTEMS CORPORATION, Otawara-Shi, Tochigi-Ken (JP)

(72) Inventors: Takahiro Ishihara, Otawara Tochigi (JP); Masao Yui, Otawara Tochigi (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 518 days.

(21) Appl. No.: 14/566,186

(22) Filed: Dec. 10, 2014

(65) Prior Publication Data

US 2015/0168523 A1   Jun. 18, 2015

(30) Foreign Application Priority Data

Dec. 16, 2013 (JP) .................. 2013-259488

(51) Int. Cl.
| | | |
|---|---|---|
| *G01R 33/54* | (2006.01) | |
| *G01R 33/48* | (2006.01) | |
| *G01R 33/565* | (2006.01) | |
| *A61B 5/055* | (2006.01) | |
| *G01R 33/28* | (2006.01) | |
| *G01R 33/58* | (2006.01) | |

(52) U.S. Cl.
CPC .......... *G01R 33/5659* (2013.01); *A61B 5/055* (2013.01); *G01R 33/288* (2013.01); *G01R 33/583* (2013.01)

(58) Field of Classification Search
CPC .................................. G01R 33/288; G01R 33/5659; G01R 33/583; A61B 5/055

USPC ......................... 324/300–322; 600/407–435; 382/128–131
See application file for complete search history.

(56) References Cited

U.S. PATENT DOCUMENTS

| | | | | |
|---|---|---|---|---|
| 5,619,138 A | * | 4/1997 | Rourke ................ | G01R 33/446 324/309 |
| 6,603,311 B2 | * | 8/2003 | Ogino .................. | G01R 33/563 324/309 |

(Continued)

FOREIGN PATENT DOCUMENTS

| | | |
|---|---|---|
| JP | 2011-011050 | 1/2011 |
| JP | 2011-120873 | 6/2011 |

(Continued)

OTHER PUBLICATIONS

JP Office Action dated Jul. 17, 2018 in JP 2014-208085.

*Primary Examiner* — Rishi R Patel
(74) *Attorney, Agent, or Firm* — Nixon & Vanderhye P.C.

(57) ABSTRACT

An MRI apparatus includes, a generating unit configured to generate radio frequency pulses applied in a pulse sequence; a sequence control unit configured to apply a radio frequency pulse related to acquisition of an image signal and a corrective radio frequency pulse during execution of one TR of a pulse sequence; and a calculation unit configured to measure the corrective radio frequency pulse and calculate a correction value for the radio frequency pulse. Based on the correction value, the generating unit corrects a radio frequency pulse related to acquisition of an image signal to be applied during a following TR later than a TR during which the corrective radio frequency pulse is measured.

14 Claims, 12 Drawing Sheets

(56) References Cited

U.S. PATENT DOCUMENTS

| | | | | |
|---|---|---|---|---|
| 6,801,037 B1 * | 10/2004 | Zhang | ............... | G01R 33/54 |
| | | | | 324/309 |
| 7,081,750 B1 * | 7/2006 | Zhang | ............... | G01R 33/54 |
| | | | | 324/309 |
| 7,990,141 B2 * | 8/2011 | Wohlfarth | ........... | A61B 5/055 |
| | | | | 324/307 |
| 8,159,221 B2 * | 4/2012 | Yui | ............... | G01R 33/5614 |
| | | | | 324/307 |
| 8,427,157 B2 * | 4/2013 | Fautz | ............ | G01R 33/246 |
| | | | | 324/307 |
| 9,329,252 B2 * | 5/2016 | Bammer | ........ | G01R 33/56341 |
| 9,599,690 B2 * | 3/2017 | Feiweier | ......... | G01R 33/4835 |
| 9,612,301 B2 * | 4/2017 | Chen | ............ | G01R 33/5613 |
| 10,054,654 B2 * | 8/2018 | Grodzki | ......... | G01R 33/543 |
| 10,175,329 B2 * | 1/2019 | Kachi | ............ | G01R 33/246 |
| 2002/0097048 A1 * | 7/2002 | Ogino | ........... | G01R 33/563 |
| | | | | 324/307 |
| 2010/0141252 A1 * | 6/2010 | Fautz | ............ | G01R 33/246 |
| | | | | 324/307 |
| 2011/0227574 A1 | 9/2011 | Akita et al. | | |
| 2013/0221965 A1 | 8/2013 | Nistler et al. | | |
| 2013/0229177 A1 * | 9/2013 | Bammer | ........ | G01R 33/56341 |
| | | | | 324/309 |
| 2015/0168523 A1 * | 6/2015 | Ishihara | .......... | G01R 33/5659 |
| | | | | 324/318 |

FOREIGN PATENT DOCUMENTS

| | | |
|---|---|---|
| JP | 2011-143235 | 7/2011 |
| JP | 2011-193989 A | 10/2011 |
| JP | 2013-144066 | 7/2013 |

\* cited by examiner

MRI APPARATUS WITH RF CORRECTED EACH TR INTERVAL

CROSS-REFERENCE TO RELATED APPLICATION

This application is based upon and claims the benefit of priority from Japanese Patent Application No. 2013-259488, filed on Dec. 16, 2013, the entire contents of which are incorporated herein by reference.

FIELD

An exemplary embodiment of the present invention relates to an MRI apparatus.

BACKGROUND

In recent years, medical imaging apparatuses (hereinafter referred to as modality apparatuses), which can collect various information about a patient less invasively, have become indispensable in health-care settings. Among others, a magnetic resonance imaging (MRI) apparatus, which involves no radiation exposure and surpasses other modality apparatus in tissue contrast resolution, has come to be used in many medical institutions. The MRI apparatus is an imaging apparatus which excites nuclear spins of a patient placed in a static magnetic field with radio frequency (RF) pulses at Larmor frequency and thereby generates an image by reconstructing a magnetic resonance signal generated from the patient as a result of the excitation. To acquire a high-contrast image with an MRI apparatus, it is necessary to tilt the nuclear spins of the patient at a desired angle by application of the radio frequency pulses. The tilt is referred to as a flip angle and magnitude of the radio frequency pulse is expressed by the flip angle. That is, to acquire a high-contrast image, accurate radio frequency pulses need to be outputted from the MRI apparatus.

The radio frequency pulses applied by the MRI apparatus is used as energy to give a tilt to the nuclear spins and other part is used as thermal energy to heat the patient and raise temperature of the patient. Thus, in the use of the MRI apparatus, from the standpoint of safety, a specific absorption ratio (SAR) has been defined as energy absorbed per unit mass of the patient and an upper limit of SAR, i.e., a safety standard value of SAR, has been prescribed as an IEC (International Electrotechnical Commission) standard (IEC 60601-2-33). More specifically, SAR (unit: W/kg) is defined as energy of the radio frequency pulses absorbed by 1 kg of living tissue, and upper limits of average SAR over arbitrary 10 seconds and average SAR over the most recent 6 minutes have been prescribed for each imaging site such as the whole body or the head. In order to carry out imaging such that the SAR will satisfy the safety standard value, the radio frequency pulses applied to the patient have to be accurate.

Thus, an MRI apparatus is provided which predicts an SAR value based on imaging conditions and optimizes a sequence of imaging protocols so as to optimize the safety standard value.

However, to carry out SAR-based safety management strictly, it is necessary to calculate the SAR value accurately. Thus, an MRI apparatus is provided which accurately calculates the SAR by directly measuring an electric current flowing through a transmitter coil by means of a scan performed prior to an examination of the patient and known as a prescan and calculating electric power used on the patient, based on the measured electric current. Furthermore, an MRI apparatus is provided which calculates an amount of power consumption from coefficients of a region, bed position, or the like by taking into consideration an amount of loss of the radio frequency pulses actually emitted to the patient, predicts the SAR value based on the calculated value, and thereby modifies imaging conditions.

In this way, techniques are provided which accurately calculate SAR values by calculating the energy emitted to the patient.

The techniques described above can calculate more accurate SAR values and strictly carry out SAR-based safety management. However, it is not known whether or not the radio frequency pulses are outputted as set out in imaging conditions, and if radio frequency pulses actually outputted are much stronger than the setting, the SAR value increases greatly, which could have resulted in a need to change the set imaging conditions. Also, even if the SAR value is measured accurately, there is a problem in that desired image contrast is not available if the radio frequency pulses are not applied at set power.

Radio frequency pulses are outputted in a pulse manner multiple times in one examination and the outputted radio frequency pulses fluctuate in real time due to heating, load changes, aging degradation, and the like of elements used in an amplifier and transmitter coil and the like of a radio frequency pulse transmission circuit. That is, actual output could deviate in real time from radio frequency pulse output expected at a time of imaging condition setting. Such deviation could cause imaging to be performed at an output higher than predicted SAR value, requiring time and effort to change the set imaging conditions, or could cause imaging to be performed at an output lower than set radio frequency pulses, making it impossible to obtain desired image contrast. Consequently, in an examination using an MRI apparatus, it is necessary that the SAR value is measured correctly and that the radio frequency pulses are applied to the patient at an output as set out in imaging conditions.

Thus, there is a demand for an MRI apparatus which can apply more accurate radio frequency pulses to the patient.

DETAILED DESCRIPTION

An MRI apparatus according to an exemplary embodiment of the present invention will be described below with reference to the accompanying drawings.

To solve the above-described problems, an MRI apparatus comprising, a generating unit configured to generate radio frequency pulses applied in a pulse sequence; a sequence control unit configured to apply a radio frequency pulse related to acquisition of an image signal and a corrective radio frequency pulse during execution of one TR of a pulse sequence; and a calculation unit configured to measure the corrective radio frequency pulse and calculates a correction value of the radio frequency pulse, wherein based on the correction value, the generating unit corrects a radio frequency pulse related to acquisition of an image signal to be applied during a following TR later than a TR during which the corrective radio frequency pulse is measured.

(1) Configuration

Figure 1:
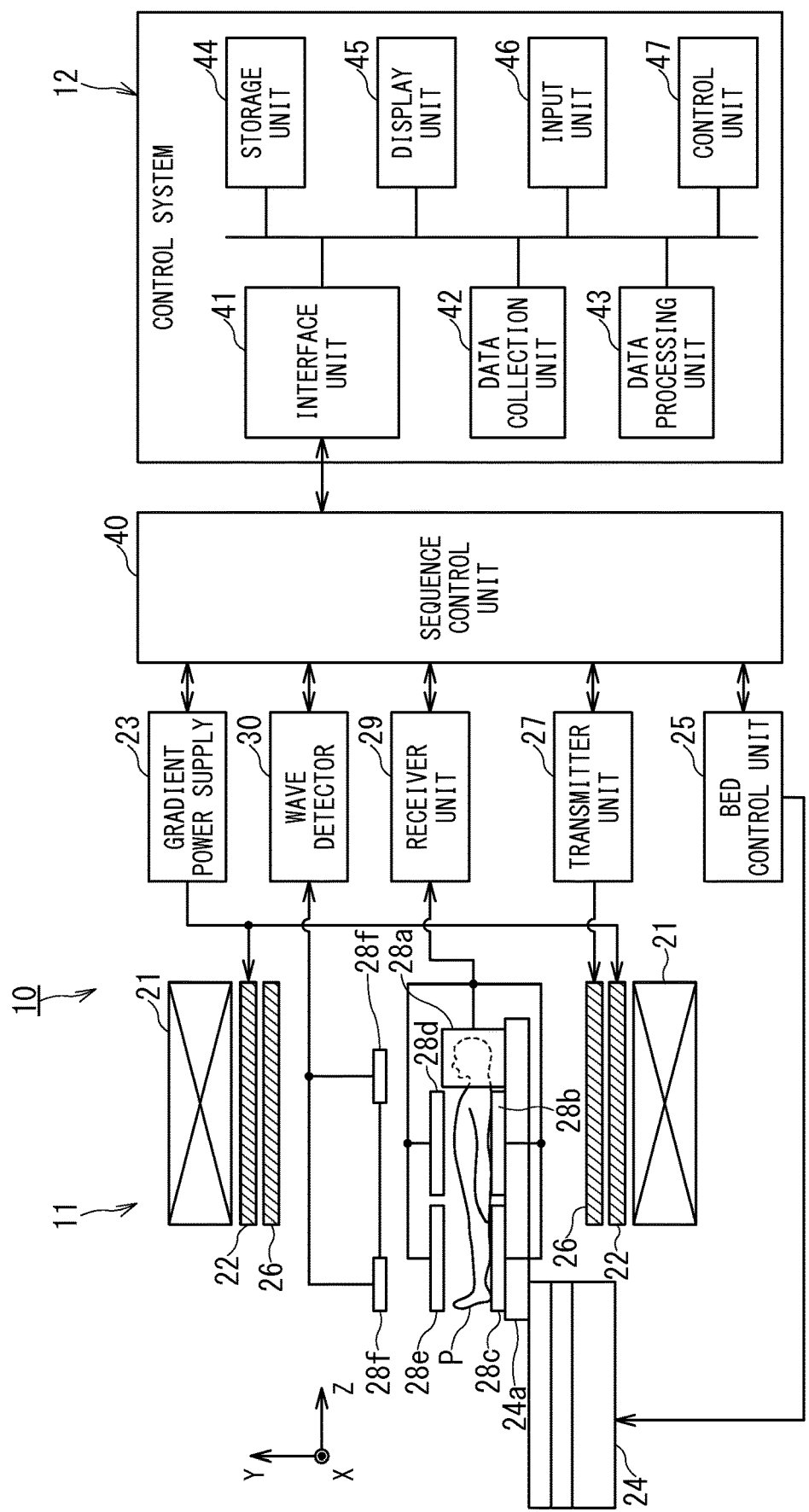
FIG. 1 is a conceptual configuration diagram showing an example of the MRI apparatus according to the exemplary embodiment.

FIG. 1 is a conceptual configuration diagram showing an example of the MRI apparatus according to the exemplary embodiment. As shown in FIG. 1, the MRI apparatus 10 is largely made up of an imaging system 11 and a control system 12.

The imaging system 11 includes a static magnet 21, a gradient coil 22, a gradient power supply 23, a bed 24, a bed control unit 25, a transmitter coil 26, a transmitter unit 27, receiver coils 28a to 28e, a pickup coil 28f, a receiver unit 29, a wave detector 30, and a sequence control unit 40 (a sequence controller).

The static magnet 21 is formed into a hollow cylindrical shape in outermost part of a gantry (not shown) and configured to generate a uniform static magnetic field in an internal space. As the static magnet 21, a permanent magnet or superconductive magnet is used, for example.

The gradient coil 22, which is formed into a hollow cylindrical shape, is placed inside the static magnet 21. The gradient coil 22 is formed by a combination of an Xch coil 22x, Ych coil 22y, and Zch coil 22z (not shown) corresponding, respectively, to X, Y, and Z axes orthogonal to one another. Being supplied with electric currents individually from the gradient power supply 23 described later, the three coils 22x, 22y, and 22z generate gradient magnetic fields whose magnetic field intensities change along the X, Y, and Z axes, respectively. Note that the Z axis coincides in direction with the static magnetic field.

The gradient magnetic fields generated on the X, Y, and Z axes by the gradient coil 22 correspond, for example, to a readout gradient magnetic field Gr, a phase encoding gradient magnetic field Gp, and a slice selection gradient magnetic field Gs, respectively. The readout gradient magnetic field Gr is used to change a frequency of an MR (magnetic resonance) signal according to spatial position. The phase encoding gradient magnetic field Gp is used to change a phase of the MR signal according to the spatial position. The slice selection gradient magnetic field Gs is used to determine an imaging section as desired.

The gradient power supply 23 supplies an electric current to the gradient coil 22 based on pulse sequence execution data sent from the sequence control unit 40.

The bed 24 includes a table top 24a on which a patient P is mounted. The bed 24 inserts the table top 24a with the patient P mounted thereon into a cavity (bore), which is an imaging area of the gradient coil 22, under the control of the bed control unit 25 described later. Normally, the bed 24 is installed such that a longitudinal direction thereof will be parallel to a center axis of the static magnet 21.

The bed control unit 25 moves the table top 24a in longitudinal and vertical directions by driving the bed 24 under the control of the sequence control unit 40.

The transmitter coil 26, which is placed on an inner side of the gradient coil 22, generates radio frequency pulses by being supplied with electric power from the transmitter unit 27.

Based on a time chart called a pulse sequence sent from the sequence control unit 40, the transmitter unit 27 controls electric power supplied to the transmitter coil 26. A power control configuration of the transmitter unit 27 will be described later.

The receiver coils 28a to 28e, which are placed on the inner side of the gradient coil 22, receive MR signals emitted from the patient P under influence of an RF magnetic field. Each of the receiver coils 28a to 28e is an array coil made up of plural coil elements which receive the respective magnetic resonance signals emitted from the patient P and outputs the received MR signals to the receiver unit 29 when the MR signals are received by the respective coil elements.

The receiver coil 28a is a head coil mounted around the head of the patient P. Also, the receiver coils 28b and 128c are spine coils placed between the spine of the patient P and the table top 124a. Also, the receiver coils 28d and 28e are abdominal coils mounted around the abdomen of the patient P. Also, the MRI apparatus 10 may be equipped with a combined transmitter-receiver coil.

The pickup coil 28f is placed inside the bore or on an outer side of the gantry for the gradient coil 22 and adapted to receive corrective radio frequency pulses outputted from the transmitter coil 26. When the pickup coil 28f receives the corrective radio frequency pulses, a resulting signal is detected by the wave detector 30. The signal detected by the wave detector 30 is converted into a digital signal by an analog-to-digital converter (not shown) and is transmitted to the control system 12 via the sequence control unit 40. Using the acquired data, the control system 12 corrects the radio frequency pulses outputted from the transmitter unit 27 and calculates the SAR value.

Based on a pulse sequence sent from the sequence control unit 40, the receiver unit 29 generates MR signal data from the receiving coils 28a to 28e.

The sequence control unit 40 is connected with the gradient power supply 23, bed control unit 25, transmitter unit 27, receiver unit 29, wave detector 30, and control system 12. The sequence control unit 40 includes a processor (not shown) such as a CPU (central processing unit) and memory, and stores control information needed to drive the gradient power supply 23, bed control unit 25, transmitter unit 27, receiver unit 29, and wave detector 30 including, for example, a pulse sequence describing operational control information such as intensity, application duration, and application timing of a pulsed current to be applied to the gradient power supply 23.

Also, the sequence control unit 40 drives the bed control unit 25 according to a stored predetermined pulse sequence and thereby moves the table top 24a forward and backward in a Z direction with respect to the gantry. Furthermore, the sequence control unit 40 drives the gradient power supply 23, transmitter unit 27, receiver unit 29, and wave detector 30 according to a stored predetermined pulse sequence and thereby controls generation and detection of an X-axis gradient magnetic field Gx, Y-axis gradient magnetic field Gy, and Z-axis gradient magnetic field Gz as well as radio frequency pulses in the gantry.

The control system 12 performs overall control of the MRI apparatus 10, data collection, and image reconstruction as well as calculation and correction of the input/output characteristics of the transmitter unit 27. The control system 12 includes an interface unit 41, a data collection unit 42, data processing unit 43, storage unit 44, display unit 45, input unit 46, and control unit 47.

The interface unit 41 is connected to the gradient power supply 23, bed control unit 25, transmitter unit 27, receiver unit 29, and wave detector 30 of the imaging system 11 via the sequence control unit 40 and adapted to control input and output of signals exchanged between the connected components and the control system 12.

The data collection unit 42 collects MR signal data transmitted from the receiver unit 29 via the interface unit 41. Upon collecting the MR signal data, the data collection unit 42 stores the collected MR signal data in the storage unit 44.

The data processing unit 43 generates spectrum data or image data of a desired nuclear spin in the patient P by applying postprocessing, i.e., a reconstruction process such as a Fourier transform, to the MR signal data stored in the storage unit 44. Also, when a locator image is captured in a prescan or the like, the data processing unit 43 generates profile data for each of the plural element coils of the receiving coils 28a to 28e based on the MR signal received by the element coil, the profile data representing a distribution of MR signals in an arranging direction of the element coil. Then, the data processing unit 43 stores various generated data in the storage unit 44.

The display unit 45 displays various information, such as spectrum data or image data, generated by data processing unit 43. As the display unit 45, a display device such as a liquid crystal display can be used.

An input unit 46 accepts various actions and information inputs from an operator. As the input unit 46, a pointing device such as a mouse or track ball, a selecting device such as a mode selector switch, or an input device such as a keyboard can be used as appropriate.

The control unit 47 measures input/output characteristics of the transmitter unit 27 based on electric power inputted in order for the transmitter unit 27 to generate radio frequency pulses and on electric power outputted to the transmitter coil 26, and thereby calculates a correction value used to control the output of radio frequency pulses for measurement at a next repetition time (TR). The TR is a time interval from the time when a radio frequency pulse is applied to excite the patient P to the time when a radio frequency pulse is applied to excite the patient P next. Furthermore, based on a signal detected by the wave detector 30 by measuring the pickup coil 28f adapted to receive an RF receive signal, the control unit 47 calculates correction values of electric power supplied to the transmitter unit 27 and transmitter coil 26. Also, the control unit 47 includes an CPU, memory, and the like not illustrated and comprehensively controls the MRI apparatus 10 by controlling the calculation of the SAR value and the components described above.

For each patient P and each imaging protocol, the storage unit 44 stores the imaging conditions necessary for generation of a pulse sequence, the MR signal data collected by the data collection unit 42, and the image data generated and SAR value calculated by the data processing unit 43 as well as correction values.

Figure 2:
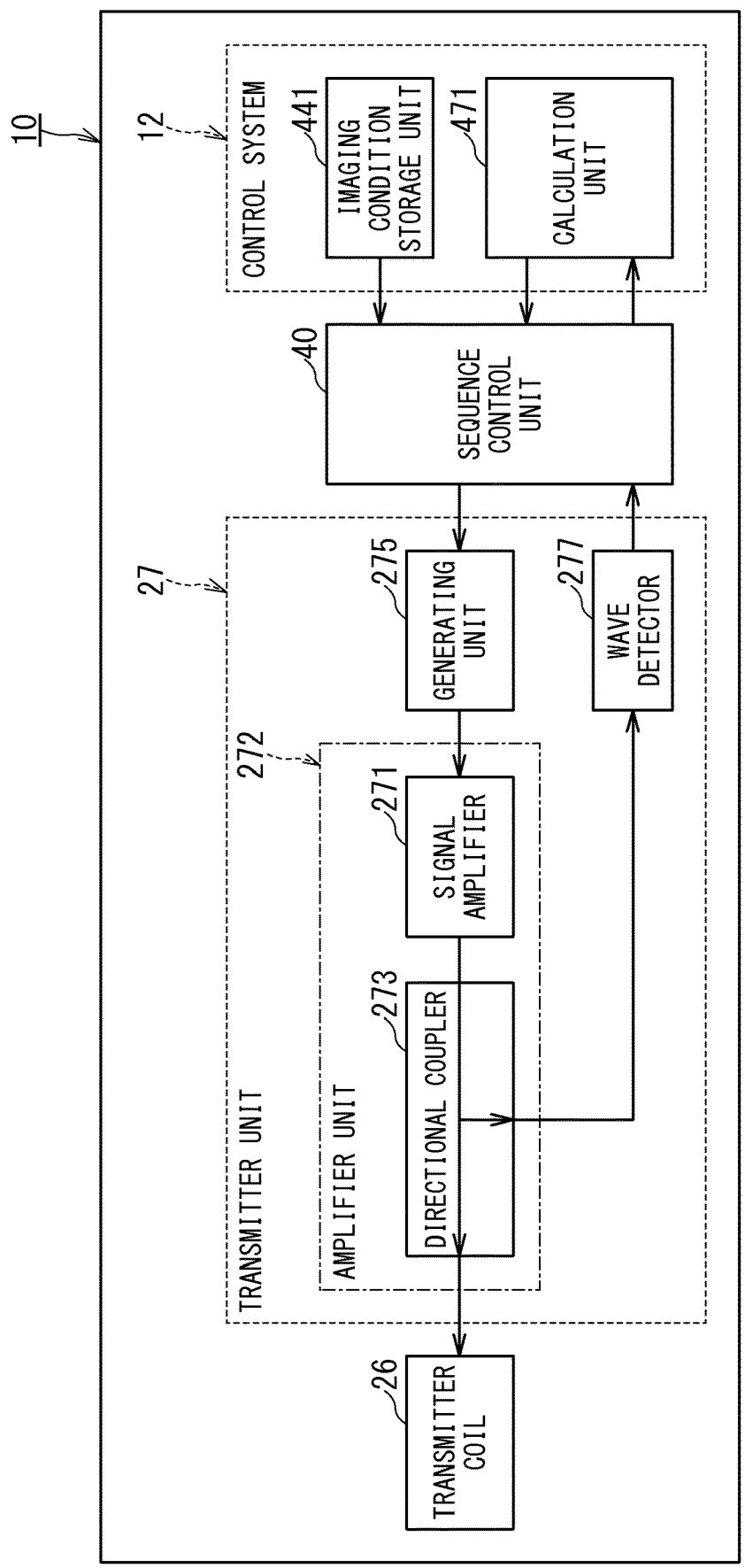
FIG. 2 is a functional block diagram showing a functional configuration example of a first embodiment of the MRI apparatus according to the exemplary embodiment.

FIG. 2 is a functional block diagram showing a functional configuration example of a first embodiment of the MRI apparatus 10 according to the exemplary embodiment. As shown in FIG. 2, the MRI apparatus 10 includes the transmitter coil 26, an amplifier unit 272, a generating unit 275, a wave detector 277, a sequence control unit 40, an imaging condition storage unit 441, and a calculation unit 471. The amplifier unit 272 includes a signal amplifier 271 and a directional coupler 273. Of these, the calculation unit 471 is a function implemented when the CPU of the control unit 47 included in the control system 12 executes a program stored in the storage unit 44.

The imaging condition storage unit 441 stores imaging conditions which prescribe a pulse sequence. The imaging conditions define a type of pulse sequence used to transmit radio frequency pulses and the like, conditions under which the radio frequency pulses are transmitted, and conditions under which MR signals are collected from the patient P. Examples of the imaging conditions include the imaging area which provides positional information in an imaging space, flip angle, repetition time (TR), number of slices, imaging site, type of pulse sequence such as an SE (Spin Echo) method or parallel imaging. The imaging site is a region of the patient P, such as the head, chest, or abdomen whose images are to be produced in the imaging area. Examples of the pulse sequence will be described later.

The generating unit 275 generates radio frequency pulses to be applied in the pulse sequence. Radio frequency pulses of a predetermined waveform are generated from reference radio frequency pulses (an RF carrier wave) according to conditions prescribed for the pulse sequence. Also, based on a correction value, the generating unit 275 corrects a radio frequency pulse related to acquisition of an image signal to be applied during a TR in a stage later than a TR during which the corrective radio frequency pulse is measured. The radio frequency pulses generated by the generating unit 275 can be either corrective radio frequency pulses for use to correct input/output characteristics such as gain and linearity of the transmitter unit 27 (hereinafter referred to simply as correction of the transmitter unit 27) or imaging radio frequency pulses for use to take images of the patient P. The radio frequency pulses generated will be described later.

The signal amplifier 271 amplifies the radio frequency pulses generated by the generating unit 275, and gives the radio frequency pulses to the transmitter coil 26 via the directional coupler 273. The amplified radio frequency pulses are transmitted to the transmitter coil 26.

The directional coupler 273 is a radio frequency device adapted to branch the radio frequency pulses transmitted from the signal amplifier 271 to the transmitter coil 26 by attenuating the radio frequency pulses using a predetermined degree of coupling (coupling coefficient). An output signal of the directional coupler 273 is detected by the wave detector 277 on an MR signal processing board and converted into a digital signal by an analog-to-digital converter (not shown). Data resulting from the conversion carried out by the analog-to-digital converter is transmitted to the control system 12 via the sequence control unit 40. The control system 12 performs correction of the transmitter unit 27 and calculates the SAR value using the acquired data.

The calculation unit 471 measures the corrective radio frequency pulses and calculates correction values of the radio frequency pulses. The calculation unit 471 receives output data of the analog-to-digital converter and calculates correction values of the transmitter unit 27. A method used by the calculation unit 471 to calculate the correction values will be described later.

The sequence control unit 40 applies a radio frequency pulse related to acquisition of an image signal and a corrective radio frequency pulse during execution of one TR of a pulse sequence. Based on input/output characteristics calculated by the calculation unit 471, the sequence control unit 40 adjusts a magnitude of the radio frequency pulses to be generated by the generating unit 275 or input power of the signal amplifier 271 in order to generate radio frequency pulses to be outputted during TRs later than the TR during which input/output characteristics are calculated.

Figure 3:
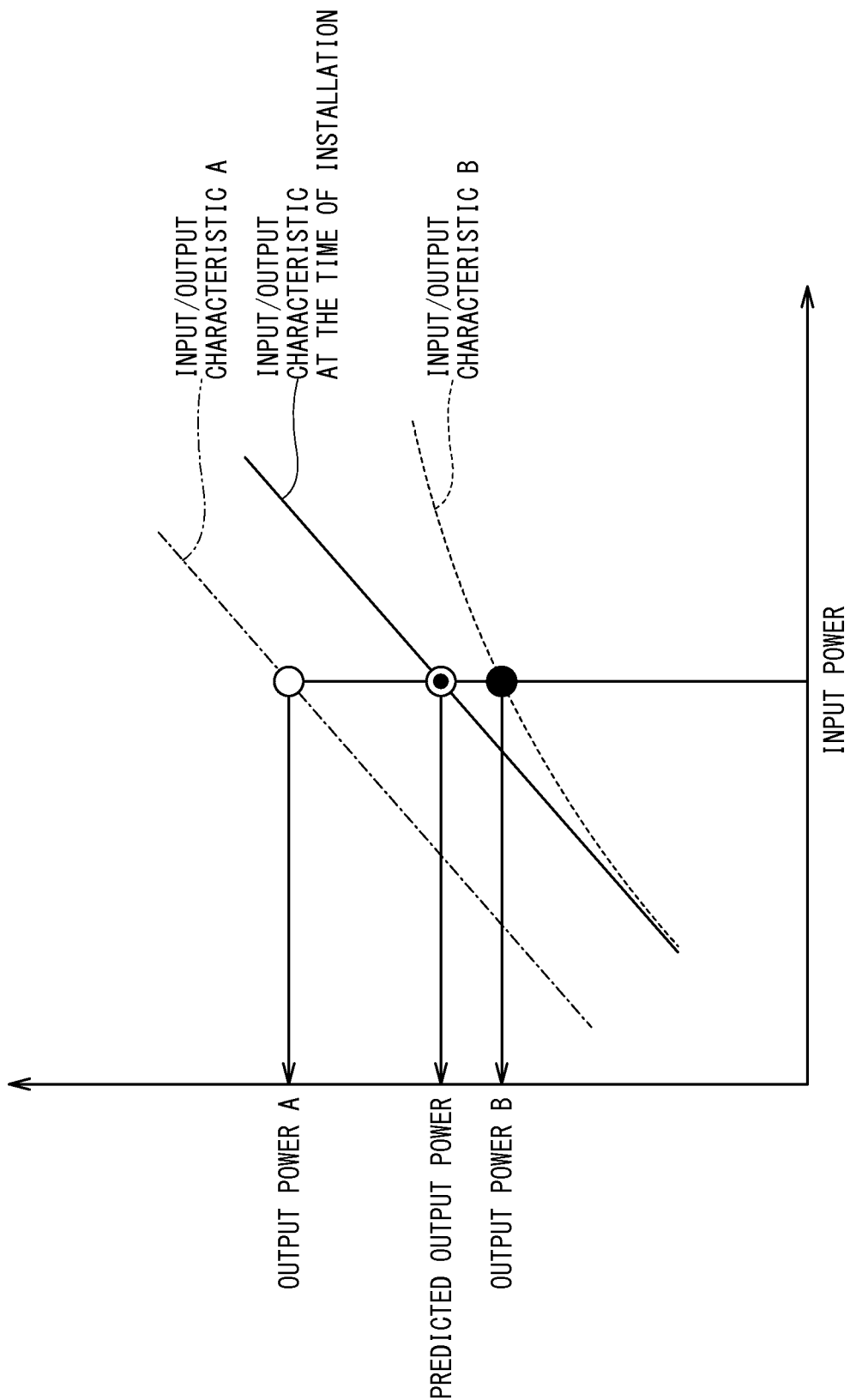
FIG. 3 is a diagram describing input/output characteristics of the transmitter unit of the MRI apparatus according to the exemplary embodiment.

FIG. 3 is a diagram describing input/output characteristics of the transmitter unit 27 of the MRI apparatus 10 according to the exemplary embodiment. Input/output characteristics of the transmitter unit 27 fluctuate due to heating, load changes, aging degradation, and the like of elements used in the signal amplifier 271 and transmitter coil 26 of a radio frequency pulse transmission circuit. Also, the electric power inputted to the transmitter coil 26 from the signal amplifier 271 varies with a balance between resistance values of the signal amplifier 271 and transmitter coil 26 and the radio frequency pulses actually transmitted may differ from output set out in imaging conditions.

The solid line in FIG. 3 represents an example of input/output characteristics of the transmitter unit 27 measured at a time of installation of the MRI apparatus 10. Input/output characteristic A indicated by alternate long and short dash lines and input/output characteristic B indicated by a broken line in FIG. 3 are examples of the input/output characteristics of the transmitter unit 27 in the MRI apparatus 10 after actual operation. According to input/output characteristic A, at the input power of the signal amplifier 271, output power A detected by the wave detector 277 is larger than predicted output power estimated from the input/output characteristic at the time of installation. On the other hand, according to input/output characteristic B, at the input power of the signal amplifier 271, output power B detected by the wave detector 277 is smaller than the predicted output power estimated from the input/output characteristic at the time of installation. Also, regarding input/output characteristic B, it can be seen that the larger the input power, the smaller a slope, resulting in an output diverging greatly from the input/output characteristic at the time of installation.

The changes in the input/output characteristics of the transmitter unit 27 shown in FIG. 3 are affected by heating of elements, changes in resistance values, and the like of the transmitter unit 27 and transmitter coil 26. Generally, in imaging on the MRI apparatus, before images start to be captured in earnest, some settings are calibrated such that imaging can be carried out properly. This calibration is referred to as a prescan. In the prescan, a sequence for calculating a center frequency of the radio frequency pulses is performed, and output of the radio frequency pulses is corrected before each examination. However, it is conceivable that changes such as shown in FIG. 3 take place moment by moment during operation of the MRI apparatus with fluctuations occurring every TR.

Thus, the MRI apparatus 10 according to the present invention measures fluctuating input/output characteristics of the transmitter unit 27 in real time and accurately outputs radio frequency pulses according to imaging conditions.

(2) Operation

Figure 4:
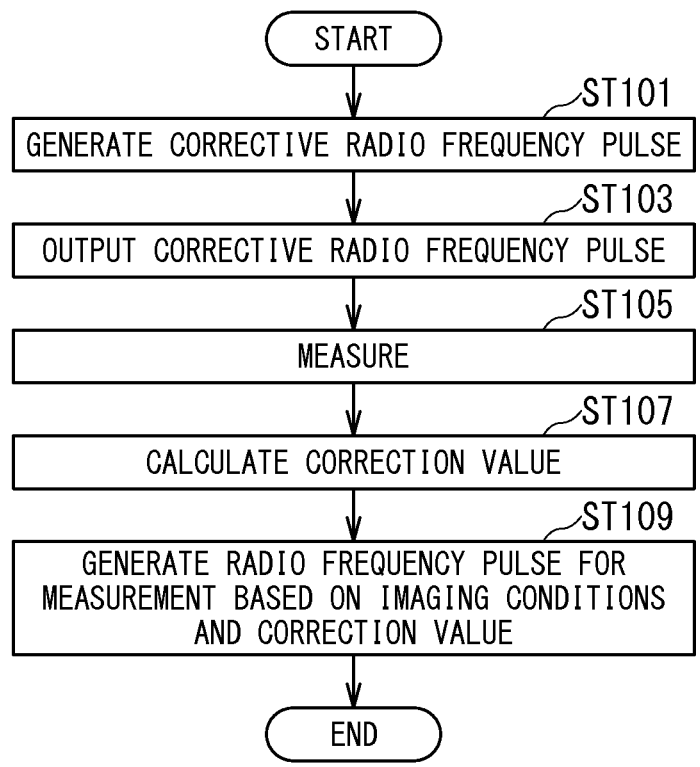
FIG. 4 is a flowchart showing an operation example of the first embodiment of the MRI apparatus according to the exemplary embodiment.

FIG. 4 is a flowchart showing an operation example of the first embodiment of the MRI apparatus 10 according to the exemplary embodiment.

In ST101 of FIG. 4, the generating unit 275 generates a corrective radio frequency pulse.

In ST103, the generated radio frequency pulse is outputted to the transmitter coil 26 via the signal amplifier 271.

In ST105, the signal outputted to the transmitter coil 26 is attenuated by the directional coupler 273 and a resulting output signal is measured by the wave detector 277 on the MR signal processing board.

In ST107, the measured signal is sent to the calculation unit 471 via the sequence control unit 40 and the input/output characteristics of the transmitter unit 27 are measured based on the measured signal to calculate a correction value.

In ST109, based on the calculated correction value, the calculation unit 471 calculates a numeric value used to correct a magnitude of the reference radio frequency pulse for use by the generating unit 275 in generating the imaging radio frequency pulse. Also, based on the calculated correction value, the input power of the signal amplifier 271 is adjusted, and the transmitter unit 27 outputs the corrected imaging radio frequency pulse.

Figure 5:
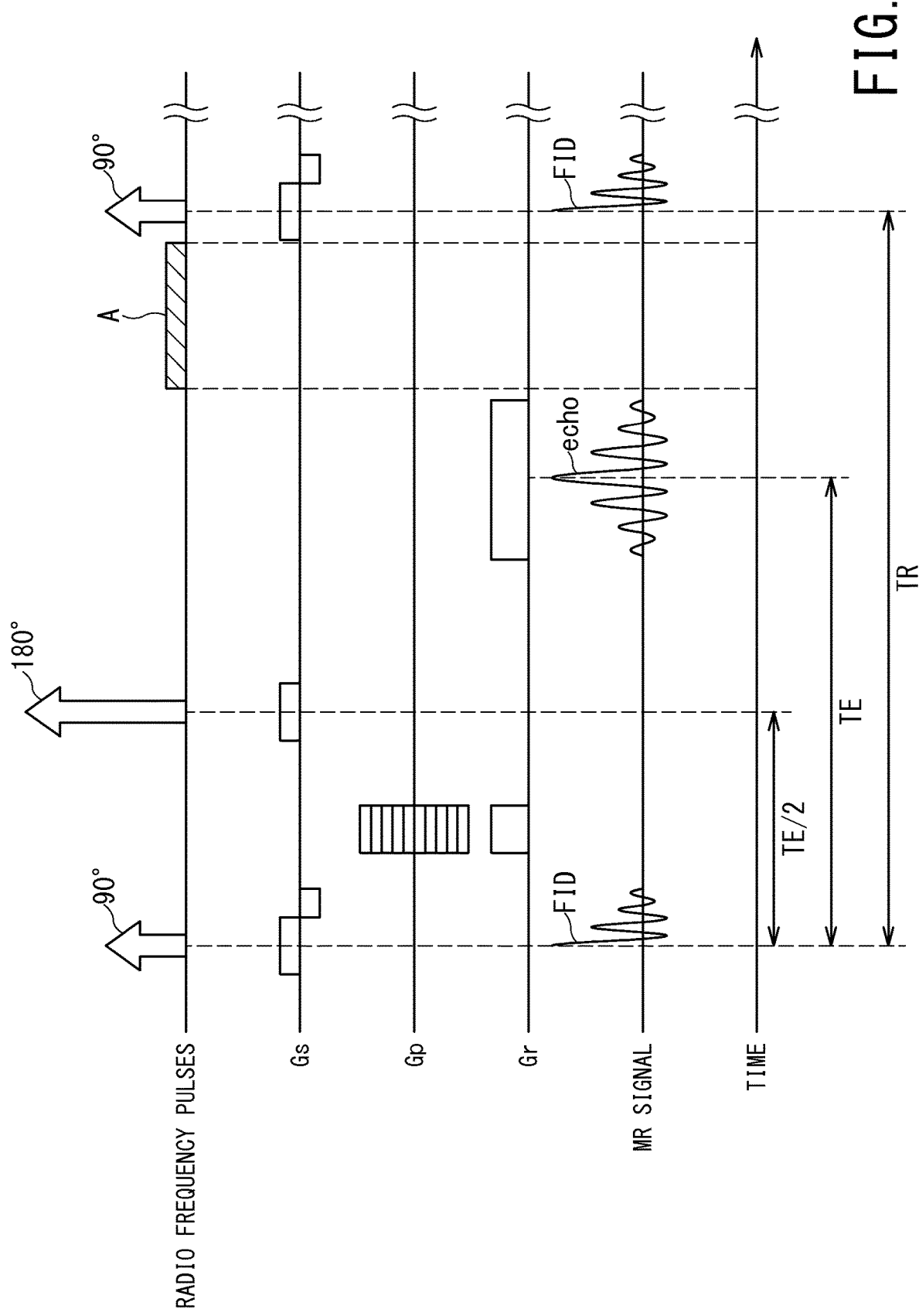
FIG. 5 is a diagram describing a possible output timing of a corrective radio frequency pulse in a pulse sequence of the SE method on the MRI apparatus according to the exemplary embodiment.

FIG. 5 is a diagram describing a possible output timing of a corrective radio frequency pulse in a pulse sequence of the SE method on the MRI apparatus 10 according to the exemplary embodiment. The chart in FIG. 5 shows a pulse sequence based on the SE (Spin Echo) method. The chart shows, from top down, radio frequency pulses, a slice selection gradient magnetic field Gs, a phase encoding gradient magnetic field Gp, a readout gradient magnetic field Gr, and an MR signal, with the arrow at the bottom representing time. The SE method uses a signal which decays as an FID (Free Induction Decay) signal after an excitation pulse is given and then returns again as an echo. Specifically, as shown in FIG. 5, if the time until an echo returns after application of an excitation pulse with a flip angle of 90 degrees is designated as an echo time (TE), a refocus pulse with a flip angle of 180 degrees is applied after a time equal to half (TE/2) the echo time. By the application of the refocus pulse, transverse magnetization which has diffused converges, and an echo signal is produced after a time of TE and received by the receiving coils 28. The SE method is an imaging method which can cancel out influence of nonuniformity of a magnetic field, and thus even if static magnetic field is slightly nonuniform or there is a substance (substance with high magnetic susceptibility) which changes a magnetic field, the method can minimize the influence thereof.

The interval TR indicated by an arrow in FIG. 5 is the repetition time. That is, in the SE method, the time between a pulse with a flip angle of 90 degrees and a next flip angle with a flip angle of 90 degrees is the TR. One examination is made up of plural imaging protocols, and one imaging protocol includes plural TRs. In one imaging protocol, the TR is repeated as many times as needed to reconstruct an image.

Region A in FIG. 5 shows an example of timing to output a corrective radio frequency pulse in a sequence according to the SE method. In this way, the sequence control unit 40 adds a corrective radio frequency pulse to part of a pulse sequence. In the pulse sequence, the corrective radio frequency pulse needs to be outputted at such a timing and output conditions that do not affect MR signals collected for image reconstruction. That is, in the SE method, a zone of influence can be moved out of an imaging region by applying a gradient magnetic field pulse with a same timing as region A. Also, the zone of influence can be moved out of the imaging region by establishing such an output condition that a frequency of a corrective radio frequency signal will not be included in an imaging band. The timing to output the corrective radio frequency pulse comes between the time immediately after MR signal collection for image reconstruction is completed and the time when a next TR starts, for example, as shown in region A of FIG. 5. When the corrective radio frequency pulse is applied at the timing described above, if a duration of the TR is made longer than when no corrective radio frequency pulse is applied, the corrective radio frequency pulse can be applied without affecting imaging in the next TR. Also, in applying the corrective radio frequency pulse, if portions irrelevant to imaging are slice-selected, influence of the corrective radio frequency pulse can be moved out of the imaging region, making it possible to apply the corrective radio frequency pulse without extending the TR. For example, in imaging the abdomen, if a gradient magnetic field is applied simultaneously such that portions such as the legs irrelevant to imaging will be selected at the timing of application of the corrective radio frequency pulse, the corrective radio frequency pulse can be applied without affecting imaging of imaging sites in the abdomen.

Figure 6A:
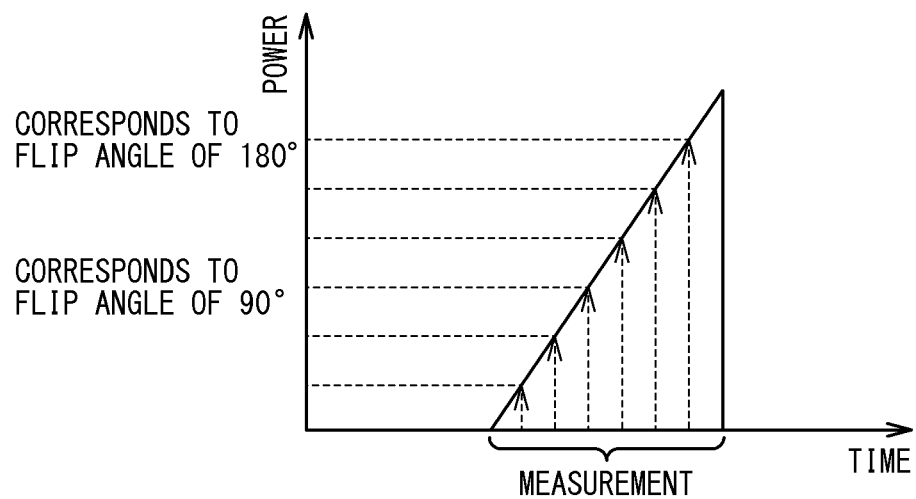
FIGS. 6A to 6C are diagrams describing a first corrective radio frequency pulse on the MRI apparatus according to the exemplary embodiment.
Figure 6B:
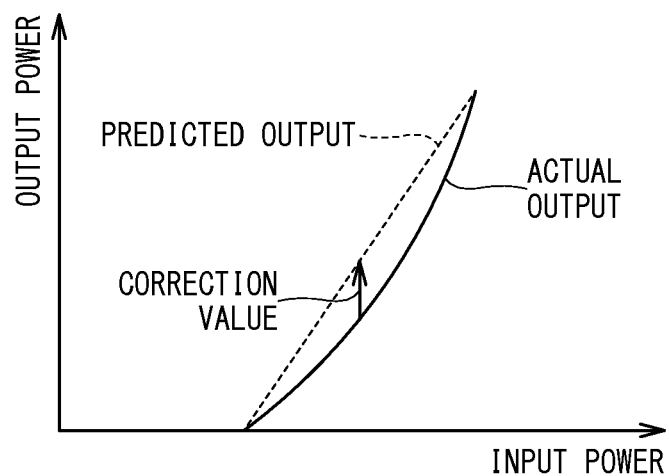
Figure 6C:
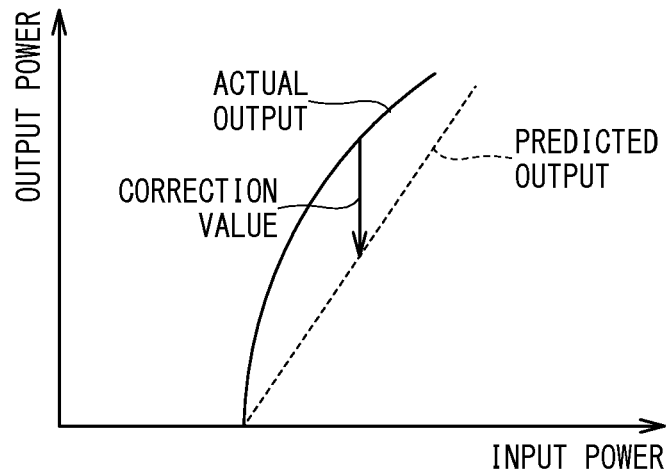

FIGS. 6A to 6C are diagrams describing a first corrective radio frequency pulse on the MRI apparatus 10 according to the exemplary embodiment. FIG. 6A illustrates a triangular wave as an example of the corrective radio frequency pulse generated by the generating unit 275. The ordinate represents electric power and the abscissa represents time. The triangular wave is outputted with an amplitude large enough to include output of an imaging radio frequency pulse. For example, the SE method illustrated in FIG. 5 outputs radio frequency pulses which contain electric power corresponding to RF outputs of at least an excitation pulse with a flip angle of 90 degrees and a refocus pulse with a flip angle of 180 degrees as imaging radio frequency pulses. Specifically, a triangular wave is outputted to supply peak power higher than the electric power supplied to the transmitter coil 26 when a radio frequency pulse with a flip angle of 180 degrees is outputted as a corrective radio frequency pulse. As shown in FIG. 6A, electric power outputted by the generating unit 275 at plural points of the outputted triangular wave and output power detected by the wave detector 277 are sampled, and the input/output characteristics of the transmitter unit 27 are measured.

Note that since output of the corrective radio frequency pulse is completed within a time as short as ten-odd ms (milliseconds), measurements can be taken in a very short time even in view of the fact that a TR interval is 1000 ms to 100 ms. Therefore, even if the patient P is irradiated with such a corrective radio frequency pulse, temperature of the patient P does not rise rapidly and the SAR value does not fluctuate much.

FIG. 6B is a graph showing an input/output characteristic of the transmitter unit 27 measured from the triangular wave illustrated by example in FIG. 6A. The ordinate represents output power and the abscissa represents input power. The solid line is a graph of output power detected by the wave detector 277 and the broken line is a graph based on output power expected from conditions set out as imaging conditions in relation to the inputted triangular wave. The graph indicated by the solid line in FIG. 6B shows an example in which output power is lower than input power, with the input power diverging greatly from predicted output in a neighborhood of a 90-degree pulse in FIG. 6A. The arrow in FIG. 6B indicates a correction value calculated by the calculation unit 471 from a difference between power outputted actually and output power predicted from input power.

As with FIG. 6B, FIG. 6C is a graph showing an input/output characteristic of the transmitter unit 27 measured from the triangular wave illustrated by example in FIG. 6A. Unlike FIG. 6B, FIG. 6C shows an example in which output power is higher than input power, with the output power growing larger than predicted output with increases in input power. As with FIG. 6B, the arrow in FIG. 6C indicates a correction value calculated by the calculation unit 471 from a difference between power outputted actually and output power predicted from input power.

Figure 7A:
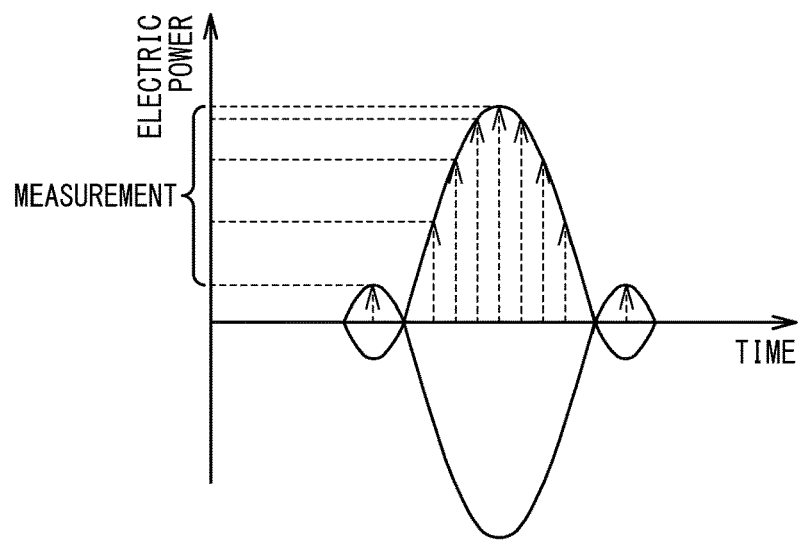
FIGS. 7A to 7C are diagrams describing a second corrective radio frequency pulse on the MRI apparatus according to the exemplary embodiment.
Figure 7B:
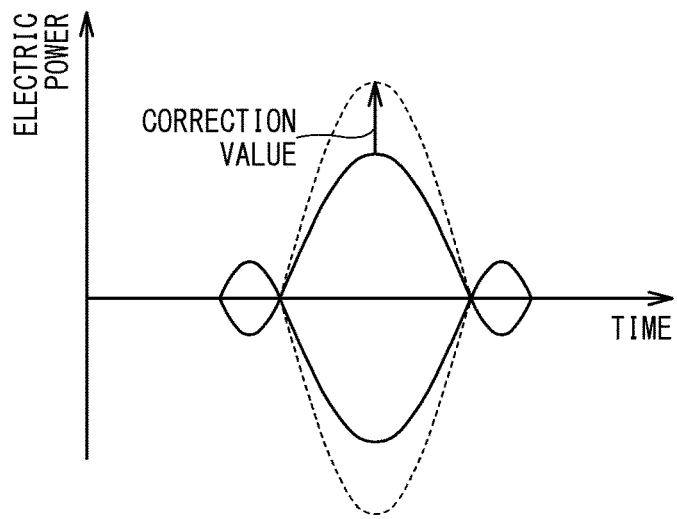
Figure 7C:
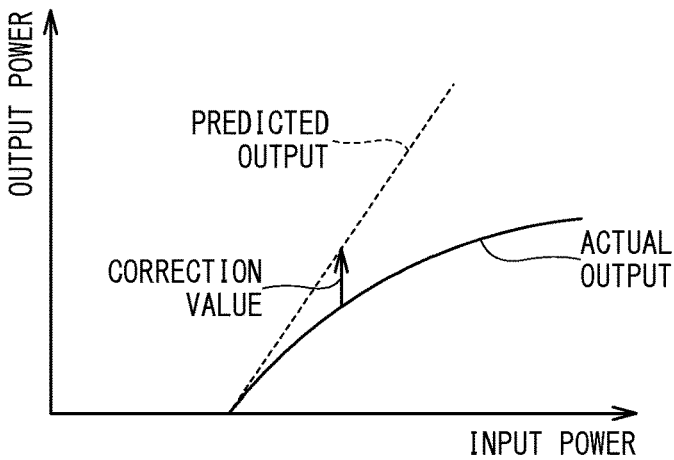

FIGS. 7A to 7C are diagrams describing a second corrective radio frequency pulse on the MRI apparatus 10 according to the exemplary embodiment. Whereas FIG. 6A shows an example in which a triangular wave is used as a corrective radio frequency pulse, FIG. 7A shows an example in which a sinc wave is used. The ordinate represents electric power and the abscissa represents time. As with the triangular wave in FIG. 6A, the sinc wave includes output of an imaging radio frequency pulse. Electric power outputted by the generating unit 275 at plural points, and output power detected by the wave detector 277 are sampled, and the input/output characteristics of the transmitter unit 27 are measured.

In FIG. 7B, the solid line indicates the sinc wave detected by the wave detector 277 and the broken line indicates the sinc wave outputted by the generating unit 275. In the example of FIG. 7B, in the portion with a large amplitude, the sinc wave actually outputted has a small amplitude. In this way, the calculation unit 471 calculates a correction value from a difference between predicted sinc wave and actually detected sinc wave.

FIG. 7C is a graph showing an input/output characteristic of the transmitter unit 27 measured from the sinc wave shown in FIG. 7A. As with FIG. 7B, the solid line indicates output power detected by the wave detector 277 and the broken line indicates output power outputted to the transmitter coil 26. As is clear from FIG. 7B, it can be seen that there is a large divergence between predicted output and actual output when the amplitude is large, i.e., when the electric power is high.

The MRI apparatus 10 described above outputs a corrective radio frequency pulse at such a timing that does not affect image reconstruction in one TR, calculates the input/output characteristics of the transmitter unit 27 from an actually outputted signal, and thereby corrects imaging radio frequency pulses in next and subsequent TRs. By measuring the input/output characteristics of the transmitter unit 27 in every TR in this way, it is possible to make corrections in the transmitter unit 27 in real time, output radio frequency pulses more faithful to imaging conditions, and thereby improve image contrast and carry out SAR-based safety management strictly.

Although the application timing of a corrective radio frequency pulse according to the SE method has been described in FIG. 5 by way of example, available timing for application of a corrective radio frequency pulse is not limited to this.

Figure 8:
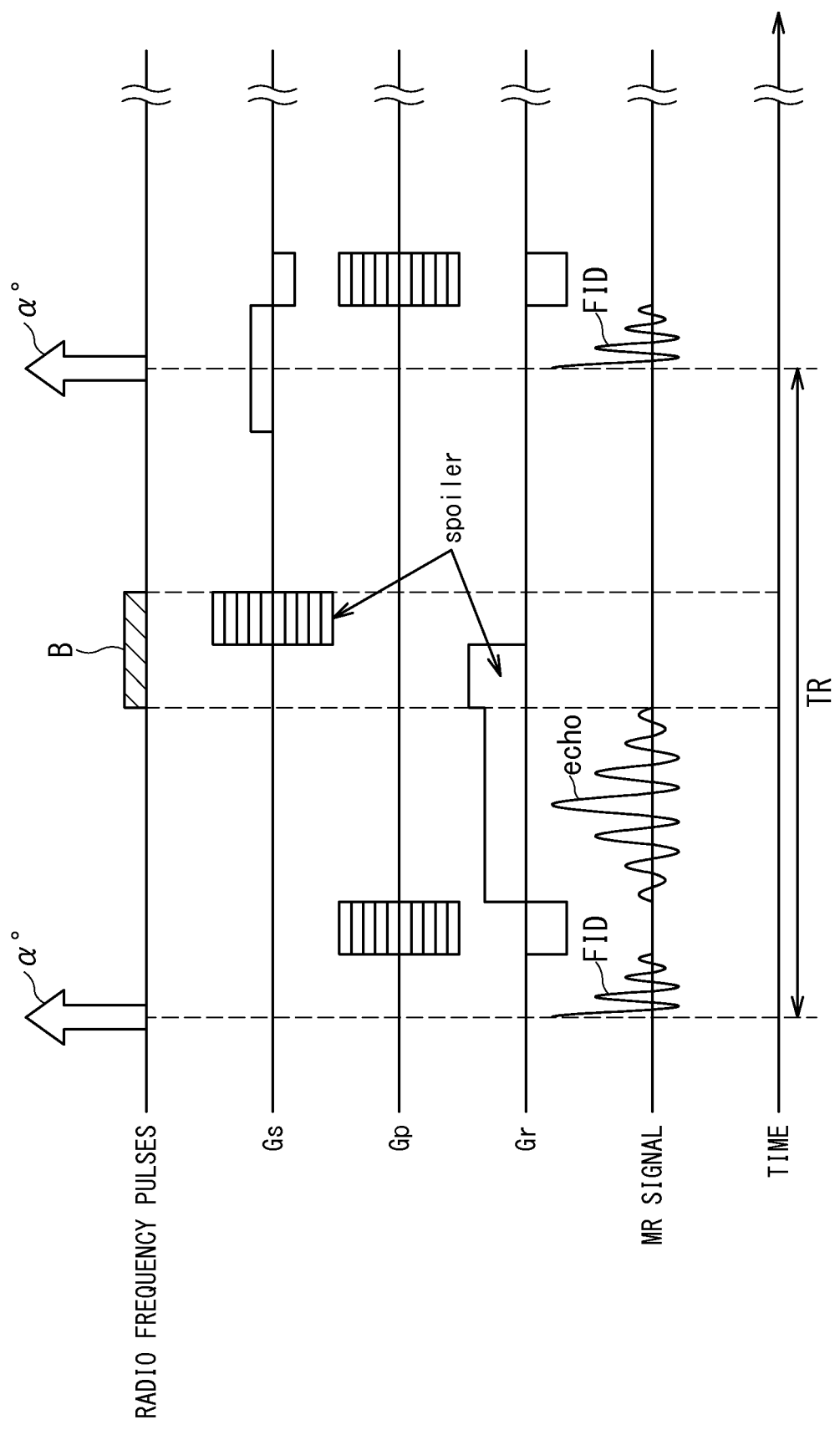
FIG. 8 is a diagram describing a possible output timing of a corrective radio frequency pulse in a pulse sequence of the GRE method on the MRI apparatus according to the exemplary embodiment.

FIG. 8 is a diagram describing a possible output timing of a corrective radio frequency pulse in a pulse sequence of the GRE method on the MRI apparatus 10 according to the exemplary embodiment. The GRE (Gradient Recalled Echo) method is a technique for obtaining an echo signal with spins aligned in phase by reversing a gradient magnetic field in a direction of a readout gradient magnetic field Gr once after excitation of spins through emission of radio frequency pulses and then applying a gradient magnetic field again in a correct direction. If a readout gradient magnetic field Gr is provided in advance and then reversed, the spins advanced in phase become slow and conversely the spins delayed in phase become fast, and consequently a diffused signal converges again to produce an echo signal. Since the method does not need to use a flip angle of 90 degrees, a recovery time can be reduced and imaging can be carried out faster than the SE method.

FIG. 8 shows a pulse sequence based on the GRE method. As with FIG. 5, FIG. 8 shows, from top down, radio frequency pulses, a slice selection gradient magnetic field Gs, a phase encoding gradient magnetic field Gp, a readout gradient magnetic field Gr, and an MR signal with the arrow at the bottom representing time. Also, the interval TR indicated by an arrow in FIG. 8 is a repetition time (TR). As described above, unlike the SE method in FIG. 5, the GRE method requires one excitation pulse and does not require a pulse with a flip angle of 90 degrees as indicated by α° in FIG. 8. Furthermore, since a refocus pulse with a flip angle of 180 degrees is not used, the influence of nonuniformity of a static magnetic field cannot be cancelled out. Thus, a method is provided which carries out imaging at high speed using a method for erasing remaining magnetization by giving a pulse called a spoiler after signal collection. With a pulse sequence of the GRE method described above, by outputting a corrective radio frequency pulse at the output timing of the spoiler pulse as shown in region B of FIG. 8, the input/output characteristics of the transmitter unit 27 can be measured without affecting a next sequence.

In the examples of FIGS. 5 and 8, sampling is done multiple times in one TR, but sampling frequency is not limited as long as sampling is done one or more times. Also, regarding sizes of corrective radio frequency pulses, pulses with a same pulse size may be outputted in respective TRs, pulses of different sizes may be outputted, or pulses may be outputted in such a manner that triangular and sinc waves are alternatively outputted for measurements. Furthermore, regarding correction timing, an acquired correction value may be reflected in an immediately succeeding TR or in a TR plural TRs after the TR in which the correction value is acquired. Also, an average value or median of correction values acquired over multiple TRs may be calculated and used to correct the radio frequency pulse.

Figures 9A, 9B:
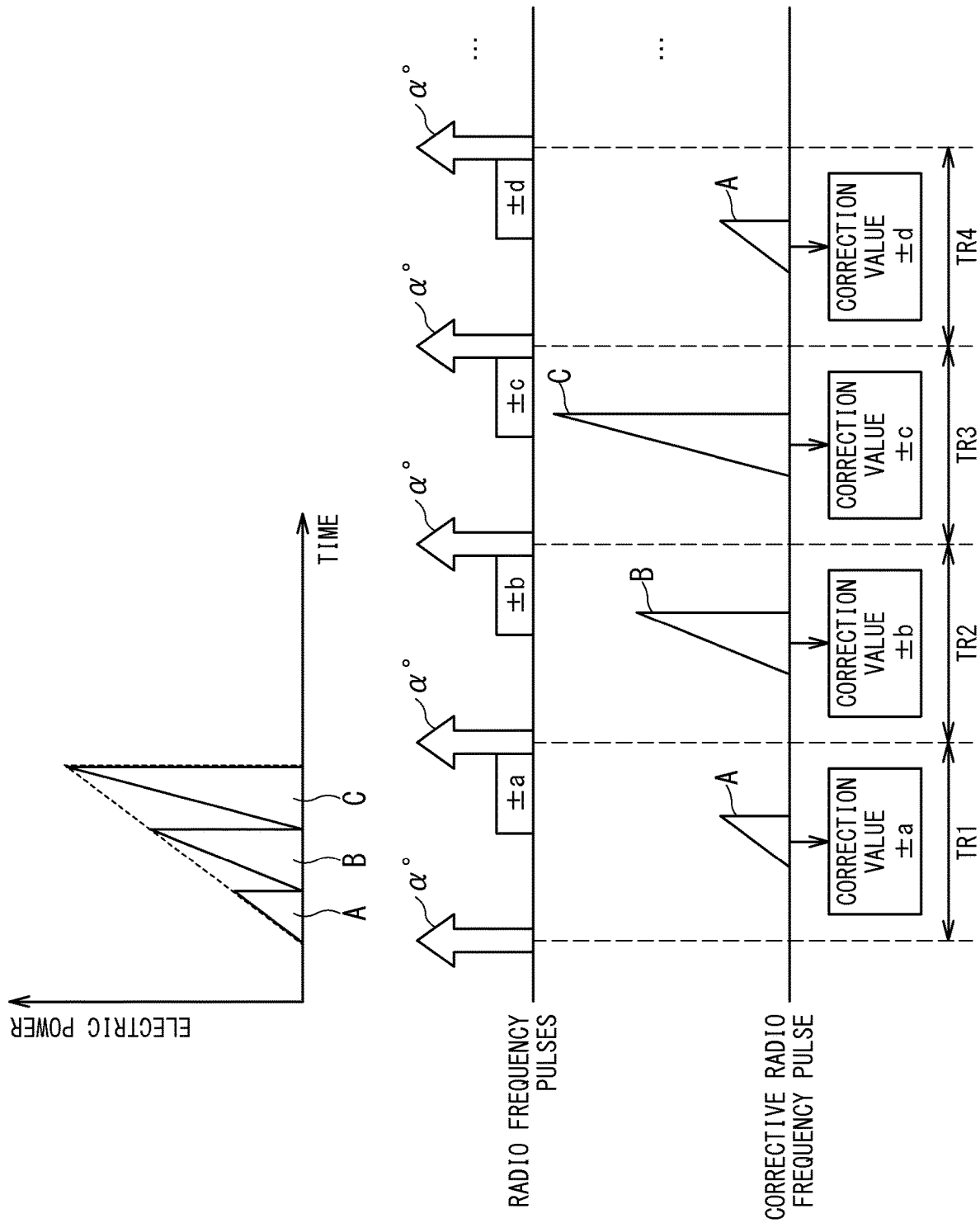
FIGS. 9A and 9B are diagrams describing a variation of the first corrective radio frequency pulse on the MRI apparatus according to the exemplary embodiment.

FIGS. 9A and 9B are diagrams describing a variation of the first corrective radio frequency pulse on the MRI apparatus 10 according to the exemplary embodiment. FIGS. 9A and 9B show an example in which the triangular wave shown in the example of FIG. 6 is outputted in various sizes over different TRs.

The triangular wave indicated by a broken line in FIG. 9A is a same one as is FIG. 6A. Each of the three triangular waves indicated by a solid line has a vertex at one of the sampling points of the triangular wave in FIG. 6A. The triangular waves are designated as triangular wave A, triangular wave B, and triangular wave C, starting from the left.

FIG. 9B shows an example in which the triangular waves A to C indicated by solid lines are outputted in different TRs. In the example of FIG. 9B, triangular wave A is outputted in TR1, triangular wave B is outputted in TR2, and triangular wave C is outputted in TR3, and triangular wave A is outputted again in TR4. In FIG. 9B, a correction value is calculated in each TR, and even though triangular waves of different sizes are outputted separately, a correction value is calculated for each triangular wave, such as a correction value of ±a in TR1, a correction value of ±b in TR2, correction value of ±c in TR3, and a correction value±d in TR4. Also, the calculated correction value may be reflected in generating an imaging radio frequency pulse in a next TR. Furthermore, correction values acquired over plural TRs may be used to correct the radio frequency pulse outputted in any of TRs subsequent to the TRs in which the correction values are acquired. Take FIG. 9B as an example, a correction value may be calculated from the correction values of ±a and ±b acquired in TR1 and TR2 and then output of a radio frequency pulse may be corrected in a subsequent TR, i.e., in TR3 or TR4. Sampling can be done multiple times on each triangular wave to measure the input/output characteristics of the transmitter unit 27. Also, even if sampling is done at one point, a correction value can be calculated by predicting actual output of desired output from a difference between planned output and actual output.

In this way, by using a method which outputs plural radio frequency pulses differing in size, it is possible to apply a signal in a shorter time than when an ordinary triangular wave or sinc wave is used. Also, for example, if frequency of a triangular wave and the sinc wave is reduced, sampling can be done more frequently, making it possible to measure input/output characteristics more accurately. Furthermore, although a triangular wave inscribed in the triangular wave of FIG. 6A is shown in FIG. 9, triangular waves in a similarity relationship with each other may be outputted in different TRs.

A method for measuring the input/output characteristics of the transmitter unit 27 by applying corrective radio frequency pulses in addition to imaging radio frequency pulses has been shown above. However, this is not restrictive, and imaging radio frequency pulses may be used as corrective radio frequency pulses. That is, as described above, even if corrective radio frequency pulses are not outputted in executing a pulse sequence, the calculation unit 471 can calculate correction values by measuring the input/output characteristics of the transmitter unit 27 based on the input power inputted to the transmitter coil 26 by the generating unit 275 and the output power detected by the wave detector 277 in relation to actual imaging radio frequency pulses.

Figure 10:
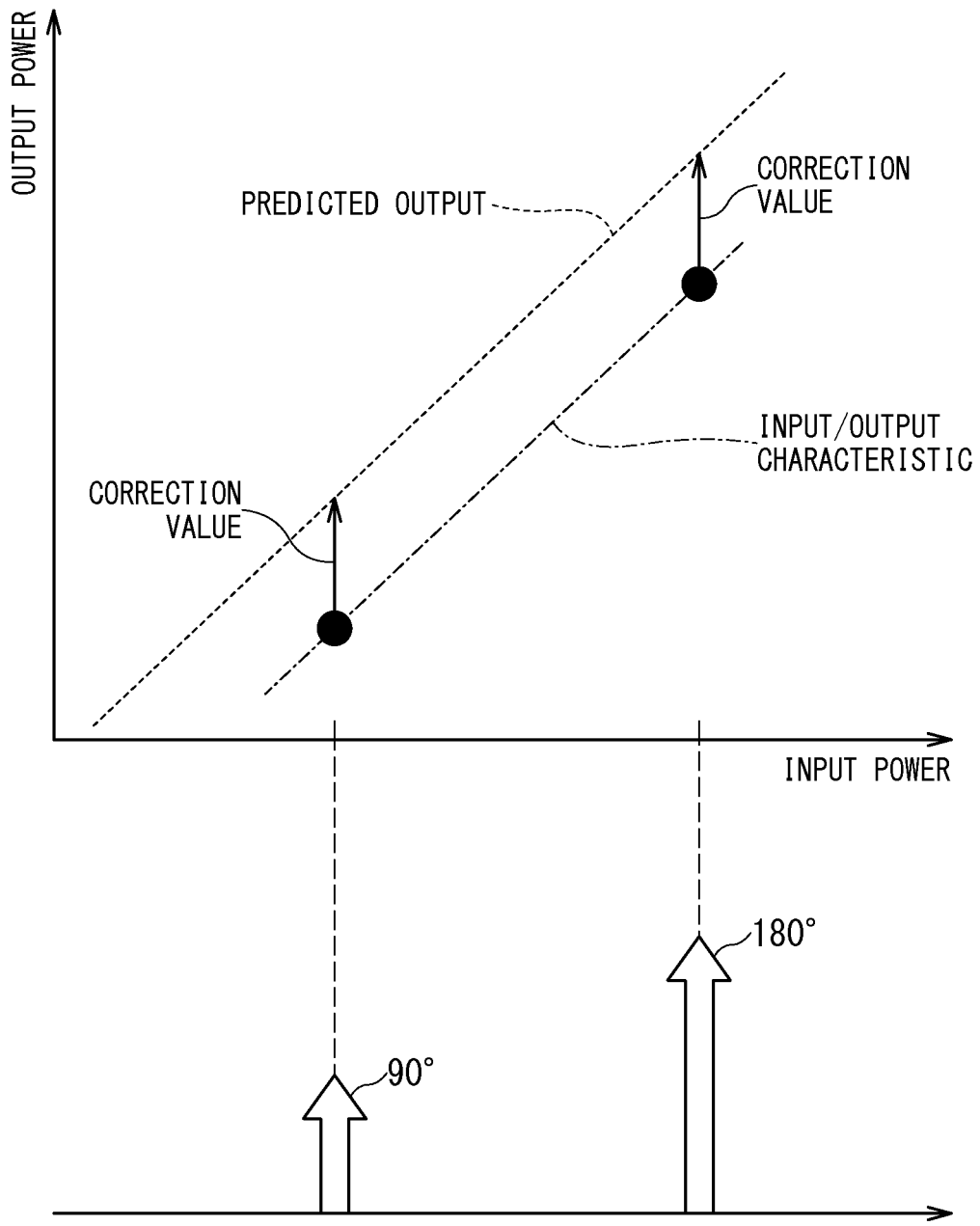
FIG. 10 is a diagram describing a method used by the MRI apparatus according to the exemplary embodiment to calculate input/output characteristics based on imaging radio frequency pulses.

FIG. 10 is a diagram describing a method used by the MRI apparatus according to the exemplary embodiment to calculate input/output characteristics based on imaging radio frequency pulses. As with FIGS. 6 and 7, FIG. 10 is a graph showing an input/output characteristic of the transmitter unit 27. The ordinate represents output power and the abscissa represents input power. The points represent output powers detected by the wave detector 277 in relation to a pulse with a flip angle of 90 degrees and a pulse with a flip angle of 180 degrees that are applied in in the SE method, respectively. The broken line represents a graph based on output power expected from conditions set out as imaging conditions. The alternate long and short dash lines show a graphic plot of a current input/output characteristic of the transmitter unit 27 based on two points measured from the pulse with a flip angle of 90 degrees and the pulse with a flip angle of 180 degrees. Respective correction values can be calculated from the two points or even if only one of the two points is detected, a correction value in another output can be predicted from a calculated correction value.

In this way, the input/output characteristics of the transmitter unit 27 are measured in each TR and accurate radio frequency pulses are applied, making it possible to carry out imaging under conditions extremely close to those set out as imaging conditions, improve image contrast, and increase accuracy of image reconstruction or image processing. Furthermore, since an accurate SAR value can be calculated in real time, imaging can be carried out in more efficient order and under more efficient imaging conditions.

Although a method for measuring the input/output characteristics of the transmitter unit 27 by measuring input power and output power using the configuration of the transmitter unit 27 has been described in the first embodiment, embodiments are not limited to this. In a second embodiment shown below, a method will be described which measures input/output characteristics of the MRI apparatus 10 based on a signal resulting from radio frequency pulses actually outputted from the transmitter coil 26 and received by a pickup coil installed near the gantry or in the bore.

Figure 11:
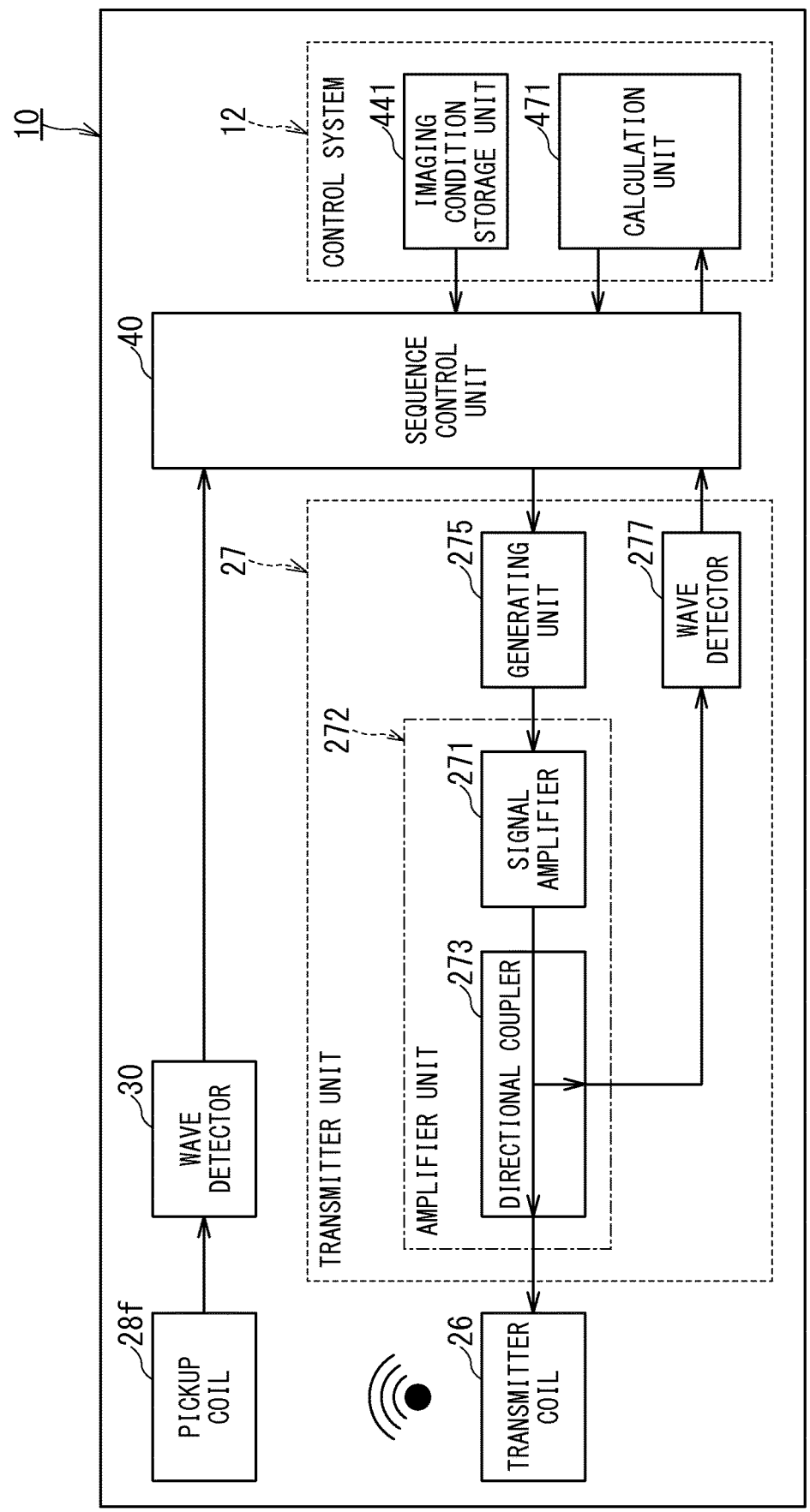
FIG. 11 is a functional block diagram showing a functional configuration example of a second embodiment of the MRI apparatus according to the exemplary embodiment of the present invention.

FIG. 11 is a functional block diagram showing a functional configuration example of a second embodiment of the MRI apparatus 10 according to the exemplary embodiment of the present invention. The same components as those in the first embodiment are denoted by the same reference numerals as the corresponding components in the first embodiment. Components different from those in FIG. 2 will only be described below.

As shown in FIG. 11, the MRI apparatus 11 according to the second embodiment includes the pickup coil 28f and wave detector 30 in addition to the components of the first embodiment.

The pickup coil 28f receives corrective radio frequency pulses outputted from the transmitter coil 26.

The wave detector 30 measures a voltage when a corrective radio frequency pulse is received by the pickup coil 28f, and acquires an output voltage. The acquired output voltage is transmitted to the calculation unit 471 via the sequence control unit 40. The calculation unit 471 calculates a correction value based on the acquired output voltage and the output voltage at which the corrective radio frequency pulse is transmitted to the transmitter coil 26 by the calculation unit 471.

Figure 12:
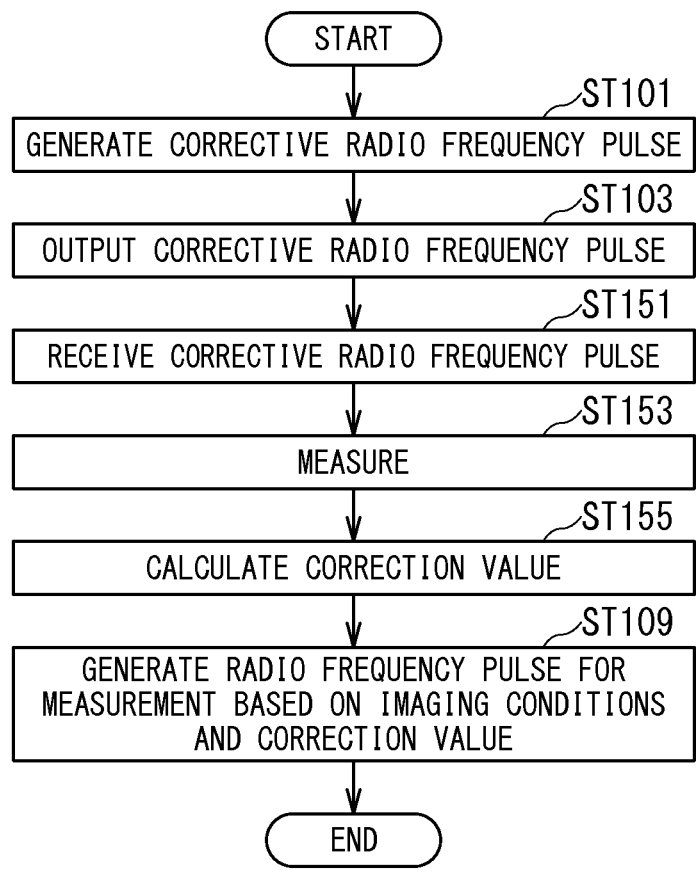
FIG. 12 is a flowchart showing an operation example of the second embodiment of the MRI apparatus according to the exemplary embodiment.

FIG. 12 is a flowchart showing an operation example of the second embodiment of the MRI apparatus 10 according to the exemplary embodiment. As with FIG. 10, the same processes as those in the first embodiment are denoted by the same reference numerals as the corresponding processes in the first embodiment. Processes different from those in FIG. 4 will only be described below.

In ST151, the pickup coil 28f receives a corrective radio frequency pulse.

In ST153, the wave detector 30 detects an output voltage.

In ST155, the calculation unit 471 calculates the input/output characteristics of MRI apparatus 10 from an input voltage inputted to the transmitter coil 26 by the generating unit 275 and an output voltage acquired by the wave detector 30, and corrects output of a next imaging radio frequency pulse.

Note that output timing of the corrective radio frequency pulse in the second embodiment is the same as the first embodiment.

In this way, by measuring actually outputted radio frequency pulses using the pickup coil 28f installed in the bore or near the gantry, the second embodiment can measure the input/output characteristics of an entire transmitter circuit system of the MRI apparatus 10 including the output from the transmitter coil 26 when compared to the first embodiment. That is, by directly measuring the radio frequency pulses applied to the patient P from the transmitter coil 26, it is possible to make corrections by taking into consideration losses and load changes in the transmitter coil 26.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An MRI apparatus comprising:
a generating unit configured to generate radio frequency (RF) pulses according to a pulse sequence, the pulse sequence including a repeating series for each of plural repetition time (TR) intervals;
a sequence control unit configured to apply an imaging RF pulse acquiring an imaging signal and a corrective RF pulse for correction following the imaging RF pulse during each TR interval of the pulse sequence thereby applying plural sets of RF pulses, each set including an imaging RF pulse and a corrective RF pulse, during each of the plural TR intervals of the pulse sequence;
a wave detector configured to detect the corrective RF pulse during each of the plural TR intervals; and
a calculation unit configured to calculate a correction value based on the detected corrective RF pulse during each TR interval,
wherein the generating unit is configured to correct an imaging RF pulse to be applied during a second and subsequent TR intervals of the plural TR intervals based on the correction value detected during earlier TR intervals in the pulse sequence.

2. The MRI apparatus according to claim 1, wherein the calculation unit calculates the correction value based on a corrective RF pulse applied when a spoiler gradient magnetic field is applied.

3. The MRI apparatus according to claim 1, wherein the calculation unit calculates the correction value based on a corrective RF pulse applied at a site outside an imaging region.

4. The MRI apparatus according to claim 1, wherein the corrective RF pulse applied to calculate the correction value is a part of an imaging sequence.

5. The MRI apparatus according to claim 1, wherein the corrective RF pulse is measured by a pickup coil, the pickup coil being a receiving coil configured to receive imaging RF pulses.

6. The MRI apparatus according to claim 1, wherein the corrective RF pulse is measured via a directional coupler configured to input the imaging RF pulses outputted from the generating unit.

7. The MRI apparatus according to claim 4 wherein a triangular wave is used as the corrective RF pulse applied to calculate the correction value.

8. The MRI apparatus according to claim 4, wherein a sinc wave is used as the corrective RF pulse applied to calculate the correction value.

9. The MRI apparatus according to claim 1, wherein the corrective RF pulse applied to calculate the correction value is outputted in an amplitude that includes a maximum value and minimum value of the imaging RF pulse.

10. The MRI apparatus according to claim 1, wherein the calculating unit calculates the correction value based on the corrective RF pulses which are different in amplitude among different TRs.

11. The MRI apparatus according to claim 1, wherein:
the calculation unit calculates a correction value each time the corrective RF pulse is outputted; and
according to the correction value, the generating unit generates a corrected imaging RF pulse by correcting the imaging RF pulse outputted in a TR interval subsequent to the TR interval in which the correction value is calculated.

12. The MRI apparatus according to claim 1, wherein:
the calculation unit calculates a correction value each time the corrective RF pulse is outputted a predetermined number of times; and
the generating unit generates a corrected imaging RF pulse by correcting output of the imaging RF pulse according to timing of calculating the correction value.

13. A magnetic resonance imaging (MRI) apparatus having provisions for limiting radio frequency (RF) heating of an imaged object to a safe specific absorption ratio (SAR) value, said apparatus comprising:
an RF generator connected to feed an imaging RF pulse acquiring an imaging signal and a corrective RF pulse for correction to at least one RF coil during execution of an MRI pulse sequence of plural repetition time (TR) intervals, the imaging RF pulse and the corrective RF pulse following the imaging RF pulse being generated during each TR interval of said plural TR intervals, thereby applying plural sets of RF pulses, each set including an imaging RF pulse and a corrective RF pulse, during each of the plural TR intervals of the pulse sequence, the pulse sequence including a repeating series for each of said plural TR intervals;
an RF signal amplitude detector positioned so as to sample and measure plural amplitudes of corrective RF outputs generated by the RF generator as a function of control inputs thereto during said MRI pulse sequence; and
SAR control circuitry connected to said RF generator and said RF signal amplitude detector, said SAR control circuitry being configured to calculate an RF pulse amplitude correction value based on a detected corrective RF pulse during a first TR interval of said plural TR intervals and which controls the RF generator in accordance with previously measured input versus output RF generator responses so as to thereafter correct the amplitude of an imaging RF pulse to be applied during a second TR interval of said plural TR intervals following the first TR interval in said MRI pulse sequence thereby more accurately and safely controlling the SAR.

14. A magnetic resonance imaging (MRI) method for limiting radio frequency (RF) heating of an imaged object to a safe specific absorption ratio (SAR) value, said method comprising:
generating and transmitting an imaging RF pulse acquiring an imaging signal and a corrective RF pulse for correction to at least one RF coil during execution of an MRI pulse sequence of plural repetition time (TR) intervals, the imaging RF pulse and the corrective RF pulse following the imaging RF pulse being generated and transmitted during each TR interval of said plural TR intervals, thereby applying plural sets of RF pulses, each set including an imaging RF pulse and a corrective RF pulse, during each of the plural TR intervals of the pulse sequence, the pulse sequence including a repeating series for each of said plural TR intervals;
sampling and measuring plural amplitudes of corrective RF outputs generated by an RF generator as a function of control inputs thereto during said MRI pulse sequence; and
calculating an RF pulse amplitude correction value based on a detected corrective RF pulse during a first TR interval of said plural TR intervals and using it to control the RF generator in accordance with previously measured input versus output RF generator responses so as to thereafter control the amplitude of an imaging RF pulse to be applied during a second TR interval of said plural TR intervals following the first TR interval in said MRI pulse sequence thereby more accurately and safely controlling the SAR.

* * * * *